US011241385B2

(12) United States Patent
Noe et al.

(10) Patent No.: US 11,241,385 B2
(45) Date of Patent: Feb. 8, 2022

(54) TOPICAL COMPOSITION AND METHOD FOR TREATING AND PREVENTING ATOPIC DERMATITIS AND INFECTIONS RELATED TO BACTERIA BIOFILM

(71) Applicant: Johnson & Johnson Consumer Inc., Skillman, NJ (US)

(72) Inventors: Sandra Noe, La Roquette (FR); Manon Rossano, Val de Reuil (FR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 76 days.

(21) Appl. No.: 16/139,363

(22) Filed: Sep. 24, 2018

(65) Prior Publication Data

US 2019/0091148 A1    Mar. 28, 2019

Related U.S. Application Data

(60) Provisional application No. 62/563,114, filed on Sep. 26, 2017.

(51) Int. Cl.
| | | |
|---|---|---|
| *A61K 9/107* | (2006.01) | |
| *A61K 9/00* | (2006.01) | |
| *A61P 31/04* | (2006.01) | |
| *A61K 47/18* | (2017.01) | |
| *A61K 47/10* | (2017.01) | |
| *A61K 47/22* | (2006.01) | |
| *A61K 47/44* | (2017.01) | |
| *A61K 47/02* | (2006.01) | |
| *A61P 17/04* | (2006.01) | |
| *A61K 47/38* | (2006.01) | |

(52) U.S. Cl.
CPC .......... *A61K 9/1075* (2013.01); *A61K 9/0014* (2013.01); *A61K 47/02* (2013.01); *A61K 47/10* (2013.01); *A61K 47/186* (2013.01); *A61K 47/22* (2013.01); *A61K 47/38* (2013.01); *A61K 47/44* (2013.01); *A61P 17/04* (2018.01); *A61P 31/04* (2018.01)

(58) Field of Classification Search
CPC ...... A61K 9/1075; A61K 47/02; A61K 47/10; A61K 47/22; A61K 47/38; A61K 47/44; A61K 9/0014; A61K 47/186; A61P 17/04; A61P 31/04
See application file for complete search history.

(56) References Cited

U.S. PATENT DOCUMENTS

| | | | | |
|---|---|---|---|---|
| 4,389,418 A | * | 6/1983 | Burton | A61K 8/416 514/785 |
| 5,885,596 A | * | 3/1999 | Parab | A61K 8/342 424/401 |
| 6,559,189 B2 | | 5/2003 | Baker, Jr. et al. | |
| 8,747,872 B2 | | 6/2014 | Baker et al. | |
| 2003/0022941 A1 | * | 1/2003 | Taylor | A01N 39/00 514/642 |
| 2004/0115159 A1 | * | 6/2004 | Tadlock | A61K 8/06 424/70.22 |
| 2006/0039942 A1 | | 2/2006 | Greten et al. | |
| 2009/0269380 A1 | | 10/2009 | Baker, Jr. et al. | |
| 2010/0226983 A1 | * | 9/2010 | Sutcliffe | A61K 8/06 424/484 |

FOREIGN PATENT DOCUMENTS

WO    WO 2010/087964 A    8/2010

OTHER PUBLICATIONS

FxSolver, Sauter mean diameter, accessed Nov. 25, 2019, pp. 1 (Year: 2019).*
Cosmetics and Toiletries, Sees Rules on Quaternary Ammonium Compounds, Feb. 12, 2012, pp. 1-2 (Year: 2012).*
Pubchem, Docosyltrimethylammonium chloride, accessed Nov. 25, 2019, pp. 1-32 (Year: 2019).*
International search report and written opinion dated Dec. 7, 2018, for international application PCT/IB2018/057369.
Davies, "A Quantitative Kinetic Theory of Emulsion Type. I. Physical Chemistry of the Emulsifying Agent", *Gas/Liquid and Liquid/Liquid Interfaces Proceedings of 2nd Congress Surface Activity*, Butterworths, London 1957, pp. 426-438, accessed at citeseerx.ist.psu.edu/viewdoc/download?doi=10.1.1.473.424&rep=rep1&type=pdf.
International Cosmetic Ingredient Dictionary and Handbook, eds. Wenninger and McEwen, pp. 1612-1613 (The Cosmetic, Toiletry, and Fragrance Assoc., Washington, D.C., 7th Edition, 1997).
O'Toole, "Microtiter Dish Biofilm Formation Assay", *Journal of Visualized Experiments* (2011)47:2437.
Zhang et al., "Characterization and antimicrobial activity of a pharmaceutical microemulsion", *International Journal of Pharmaceutics* (2010) 395:154-160.

* cited by examiner

*Primary Examiner* — Andrew S Rosenthal
*Assistant Examiner* — Lyndsey M Beckhardt
(74) *Attorney, Agent, or Firm* — Michelle A. Cristaldi

(57) ABSTRACT

A nanoemulsion containing a quaternary ammonium salt with at least a twenty carbon chain is effective to prevent the growth of biofilms.

8 Claims, No Drawings

TOPICAL COMPOSITION AND METHOD FOR TREATING AND PREVENTING ATOPIC DERMATITIS AND INFECTIONS RELATED TO BACTERIA BIOFILM

CROSS-REFERENCE TO RELATED APPLICATIONS

This application claims the benefit of U.S. provisional application 62/563,114 filed on Sep. 26, 2017, the complete disclosure of which is hereby incorporated herein by reference for all purposes.

FIELD OF THE INVENTION

The present invention relates to the treatment and prevention of atopic dermatitis and infections related to bacteria biofilm. More precisely the invention discloses a topical composition for inhibiting *Staphylococcus aureus* bacteria associated with biofilm found in atopic dermatitis. A method of treatment of the skin or mucosa, and use of said topical composition are disclosed.

BACKGROUND OF THE INVENTION

Atopic dermatitis, also named eczema syndrome, is a chronic relapsing pruritic inflammation of the skin that can compromise quality of life. Atopic dermatitis affects 10-20% of children and 1-3% of adults worldwide with increasing prevalence in highly industrialized countries. Atopic dermatitis is characterized by an impaired epidermal barrier, dysregulation of innate and adaptive immunity, and a high susceptibility to bacterial colonization and infection. Hence, lubricants (ointments & creams) and topical or oral corticosteroids, which act on the immune system by blocking the production of substances that trigger allergic and inflammatory actions, remain the first-line treatments. Similarly, antihistamine can also be administrated. If pruritus does not respond to standard treatments, antibiotics might be considered.

Lubricants are effective in keeping the skin hydrated and repairing the skin barrier. However, the cosmetic acceptance of these types of formulations may be poor which is reflected in a lower compliance among the atopic dermatitis patients. Moreover, this approach is often not sufficient by itself. Corticosteroids on the other hand are powerful medications but are known to induce side effects, some of which might be severe in case of long term usage. While antihistamine can be used to treat itch associated with atopic dermatitis, they can cause sleepiness and may not help in all cases of atopic dermatitis. Finally, the use of antibiotics is controversial due to the raising occurrence of bacterial resistance.

Since atopic dermatitis is also characterized by an altered skin microflora, some researchers investigated the role of bacteria in atopic dermatitis. More generally, nanoemulsions have been reported to have strong bactericidal activity and could therefore be of interest in the treatment of atopic dermatitis.

However, no physico-chemical correlation has been studied to understand which parameter is responsible for the activity. The action mode is not yet clearly clarified, but it seems that the surfactants used to stabilize the nanoemulsions can modulate the antimicrobial activity of the nanoemulsion.

U.S. Pat. No. 6,559,189 (Baker) teaches the use of nanoemulsions for killing or inhibiting the growth of pathogenic agents. Nanoemulsions according to Baker comprise surfactants, detergents and cationic halogen containing compounds. Baker discloses a long list of possible formulations and quaternary ammonium compounds in the formulations. None of the quaternary ammonium compounds have an alkyl linear chain greater than 18 carbon atoms. The most effective compositions according to Baker contain detergents such as Tween, Triton and Tyloxapol. Use of these detergents on damaged skin (atopic dermatitis) would cause irritation and discomfort to the patient. Finally, Baker remains silent about biofilms and the possible use of nanoemulsion on established or growing bacterial biofilms.

U.S. Pat. No. 8,747,872 (Baker) teaches the use of nanoemulsion for the treatment of bacteria associated with biofilms such as found in pulmonary infections. Among the many embodiments for nanoemulsion formulation disclosed, some may contain quaternary ammonium salts. None of the disclosed quaternary ammonium salts has an alkyl linear chain superior to 18 carbon atoms. Examples provided by Baker of formulations effective on biofilm comprise: poloxamer, ethanol and cetylpyridinium chloride ($P_{407}5EC$), or tween80, ethanol and cetylpyridinium chloride ($W_{80}5EC$). Uses of such formulations could cause irritation and discomfort to the patient if used on damaged skin (atopic dermatitis).

A need exists to find topical compositions to treat or prevent the growth of pathogens on the skin of atopic dermatitis patients that would not have the side effects of the solutions already known in the art. There is also a need for preventing or slowing the growth of biofilms including biofilms related to skin diseases.

Surprisingly, the inventors have found that nanoemulsions of quaternary ammonium salts with a long alkyl chain can overcome the drawbacks of the prior compositions.

SUMMARY OF THE INVENTION

As used herein, unless otherwise specified, all percentages are by weight based on the total weight of composition referred to. The disclosures of all patents and published applications referred to herein are incorporated by reference in their entirety.

As used herein, "substantially free" of an ingredient means containing about 5% by weight or less of that ingredient. Preferably, substantially free of an ingredient means containing about 2% or less, or about 1% or less, or about 0.5% or less or about 0.1% or less, or about 0.05% or less, or about 0.01% or less, by weight of such ingredient. In certain embodiments, substantially free of an ingredient means completely free of the ingredient, i.e., containing none of that ingredient.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein. As used herein, "cosmetically/dermatologically acceptable" means that the ingredients which the term describes are suitable for use in contact with tissues (e.g., the skin or hair) without undue toxicity, incompatibility, instability, irritation, allergic response, and the like.

By "inhibit" or other forms of inhibit, such as "inhibiting" or "inhibition," is meant to hinder or restrain a particular event or characteristic or to decrease the frequency or severity of a particular event or characteristic. It is understood that this is typically in relation to some standard or expected value, in other words it is relative, but that it is not always necessary for the standard or relative value to be referred to. For example, "inhibits biofilm formation" means hindering or restraining the formation or further growth of a biofilm or decreasing the severity of biofilm formation relative to a standard or a control.

By "prevent" or other forms of prevent, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce or inhibit. As used herein, something could be reduced but not inhibited or prevented, but something that is reduced could also be inhibited or prevented. Also, something could be inhibited but not reduced or prevented, but something that is inhibited could also be reduced or prevented. Likewise, something could be prevented but not inhibited or reduced, but something that is prevented could also be inhibited or reduced. It is understood that where reduce, inhibit, or prevent are used, unless specifically indicated otherwise, the use of the other two words is also expressly disclosed. Thus, if reduces biofilm formation is disclosed, then inhibits and prevents biofilm formation are also disclosed, and the like.

The present invention is directed to a topical composition including an oil in water nanoemulsion. The nanoemulsion included a quaternary ammonium salt surfactant having at least one linear alkyl chain of at least 20 carbon atoms, an oil phase including at least one emollient; and a water phase. The quaternary ammonium salt surfactant is selected from the group consisting of behentrimonium chloride, behenalkonium chloride, dibehenyldimonium chloride, behenamidopropylethyldimonium ethosulfate and mixtures of these surfactants. In a preferred embodiment, the quaternary ammonium salt surfactant is behentrimonium chloride. The quaternary ammonium salt surfactant can be trimethyl quaternary ammonium salt.

The surfactant in the nanoemulsion is in an amount from about 1% to about 7% by weight of the composition or from about 2% to about 5% by weight of the composition. The nanoemulsion has droplets having a Sauter diameter D[3;2] below about 120 nm or droplets having a Sauter diameter D[3;2] between about 10 nm and about 100 nm or having a Sauter diameter D[3;2] between about 30 nm to about 70 nm.

The composition of the present invention can have a viscosity below 700 cP or more preferably below 360 cP at 45 $s^{-1}$ when measured by a Physica MCR 300 (Anton Paar GmbH) at a shear rate of 45 $s^{-1}$ a viscosity below 125 cP when measured in the same manner. The composition can contain an emollient is in an amount from about 1% to about 15% by weight of the composition and a rheology modifier in an amount from about 0.5% to about 5% by weight of the composition. The rheology modifier is selected from the group consisting of cetyl alcohol, stearyl alcohol, carnauba wax, stearic acid, hydroxyethylcellulose, guar gum, locust bean gum, xanthan gum, gelatin, silica, bentonite, magnesium aluminum silicate, carbomers and mixtures thereof.

The topical composition further included at least one humectant in an amount from about 5% to about 15% by weight of the composition; and bout 5% to about 15% by weight of water, or about 50% to about 90% by weight of water. In a preferred embodiment, the composition is free of additional surfactants and of a preservative.

The present invention is also directed to a method of killing or inhibiting the growth of bacteria in a biofilm comprising exposing a biofilm to the nanoemulsion according to the present invention. An example of the biofilm is *Staphylococcus aureus*.

DETAILED DESCRIPTION OF THE INVENTION

The Nanoemulsions

The nanoemulsions according to the present invention are water in oil emulsions that contain a quaternary ammonium salt surfactant having at least one linear alkyl chain of at least 20 carbon atoms.

The oil phase of the nanoemulsion can include, hydrocarbon oils such as paraffin oil, purcellin oil, perhydrosqualene, microcrystalline wax, petrolatum, mineral oil (Paraffinum liquidum), polyalkene, cerasin, ozokerite, polyethylene, perhydrosqualene, poly alpha olefin, hydrogenated polyisobutene, beeswax, and mixtures thereof; saturated esters such as isopropyl palmitate, alkyl myristates such as isopropyl, butyl and cetyl myristates, hexodecyl stearate, ethyl palmitate, octanoic and decanoic acid triglycerides and cetyl ricinoleate, Sodium Formate, Tocopheryl Acetate, Butyl Acetate, Ethyl Acetate, Methoxyisopropyl Acetate, Glyceryl Laurate, PEG-30 Glyceryl Laurate, Potassium Laurate, Glyceryl Myristate, Isopropyl Myristate, Potassium Myristate, Propylene Glycol Myristate, Zinc Myristate, Ascorbyl Palmitate, Cetyl Palmitate, Isopropyl Palmitate, Potassium Palmitate, Retinyl Palmitate, Acetylated Glycol Stearate, Ethylhexyl Stearate, Glyceryl Isostearate, Glyceryl Stearate, Glyceryl Stearate SE, Glycol Distearate, Magnesium Stearate, PEG-150 Distearate, PEG-3 Distearate, PEG-30 Glyceryl Stearate, PEG-32 Stearate, PEG-6 Stearate, Polyglyceryl-2 Diisostearate, Polyglyceryl-3 Distearate, Potassium Stearate, unsaturated esters Potassium Sorbate, Glyceryl Oleate, Ethyl Linoleate, Glyceryl Linoleate, Tocopheryl Linoleate; silicone oils such as dimethylpolysiloxane, methylphenylpolysiloxane and silicone-glycol polymer; vegetable oils comprising linoleic acid triglycerides such as Cocos Nucifera (coco oil), Elaeis Guineensis Oil (palm oil), Arachis Hypogaea (arachide oil), Argania Spinosa (argan oil) sweet almond oil, avocado oil, calophyllum oil, lanolin, castor oil, Olea Europaea olive oil, Triticum Vulgare wheat germ oil, maize germ oil, soybean oil, sunflower oil, cottonseed oil, Lucerne oil, poppy oil, red kuri oil, Sesamum Indicum sesame oil, rapeseed oil, evening primrose oil, millet oil, barley oil, quinoa oil, rye oil, safflower oil, candlenut oil, passionflower oil, grape seed oil, rapeseed oil, tall seed oil, flaxseed oil, peanut oil, buckthorn oil, blackcurrant seed oil, Siberian pine seed oil, primrose oil, Glycine Soja, Corylus Avellana (Hazel oil), Juglans Regia (nut oil), Vitis Vinifera (Grape oil).

The oil phase of the nanoemulsion includes about 5% to about 40% or about 10% to about 30% or about 10% to about 20% by weight percent of the nanoemulsion.

The aqueous phase of the nanoemulsion can include about 60% to about 95% of the nanoemulsion, or about 70% to about 90% or about 80% to about 90% weight percent of the nanoemulsion. A preferred ratio of oil phase to water phase in the nanoemulsion is 1:9.

The surfactant used in the nanoemulsion is a quaternary ammonium salt having at least one linear alkyl chain with a least 20 carbon atoms. The quaternary ammonium salt surfactant may be selected from the list comprising behentrimonium chloride, behenalkonium chloride, dibehenyldimonium chloride, behenamidopropylethyldimonium ethosulfate or mixtures thereof. In a particular embodiment, the quaternary ammonium surfactant stabilizing the nanoemulsion according to the present invention may be further characterized by having only one linear alkyl chain consisting of more than 5 carbon atoms. The ammonium salt surfactant used in the present invention is a trimethyl quaternary ammonium salt.

The nanoemulsion according to the present invention can include emollients. The emollient can be selected from the group comprising petrolatum, isopropyl palmitate, vegetable oils whether or not hydrogenated, silicone oils, any liquid polymerized siloxane such as dimethicone, cyclomethicone, cyclopentasiloxane, diméthiconol and amodimethicone, mineral oil, waxes such as parrafin, paraffinum liquidum, and petrolatum, aloe vera, fatty alcohols such as arachidyl alcohol, batyl alcohol, behenyl alcohol, C12-13 alcohols, cetearyl alcohol, cetyl alcohol, coconut alcohol, isocetyl alcohol, octyldodecanol and palm alcohol, fatty acids and esters of fatty acids such as batyl stearate, cetearyl behenate, cetearyl isononanoate, cetyl esters, coconut acid, ethyl linoleate, ethyl linolenate, ethyl olivate, ethylhexyl cocoate, ethylhexyl myristate, glyceryl caprylate, glyceryl laurate/oleate, glyceryl ricinoleate, isocetyl salicylate, isostearyl alcohol, linoleic acid, linolenic acid, oleic acid, palm kernel acid, palmitic acid and wheat germ acid, shea butter (Butyrospermum parkii butter), cocoa butter (Theobroma cacao butter), waxes, derivatives of glycerides such as capric/caprylic triglyceride, cocoglycerides, and palm glycerides, cholesterol, lanolin and derivatives, derivatives of PEGs, squalane, squalene, sucrose and derivatives, glycerol derivatives such as glycerol trioctanoate:tricaprylin, glycerol, tristearate:tristearin, and mixtures thereof. The emollient may be in the composition from about 1% to about 15% by weight of the composition.

The nanoemulsions can include humectants selected from pyrrolidone carboxylic acid (PCA) and derivatives (arginine PCA, chitosan PCA, copper PCA, ethylhexyl PCA, lauryl PCA, magnesium PCA, sodium PCA, zinc PCA) butylene glycol, calcium gluconate, fructose, glucose, isomalt, lactose, maltitol, mannitol, polydextrose, sorbitol, sucrose, xylitol, glycerol, glycyrrhizic acid and derivatives, histidine, hyaluronic acid and its salts (sodium hyaluronate), hydrolysates of silk, keratin or soya, PEG (-7, -8, -10, -12, -14), phytantriol, propylene glycol, silk (serica), urea and mixtures thereof. The at least one humectant can be in the composition in an amount from about 5% to about 15% by weight of the composition.

The nanoemulsion can include a booster to enhance the antimicrobial activity of the surfactant. These boosters can be butyl glycol, propylene glycol and capryl glycol in an amount from about 0.05 to 2.0%.

The nanoemulsion can include a rheology modifier in an amount form about 0.5% to about 5% by weight of the topical composition. The rheology modifier may be selected form the list consisting of cetyl alcohol, stearyl alcohol, carnauba wax, and stearic acid, vegetable gums (hydroxyethylcellulose, guar gum, locust bean gum, xanthan gum), and gelatin, silica, bentonite, and magnesium aluminum silicate, carbomers (polyacrylic acids) and mixtures thereof.

The nanoemulsions of the present invention are made by mixing the oil and aqueous phases using high shear force blenders known in the art. The nanoemulsion has droplets having a Sauter diameter D[3;2] below preferably below 200 nm, more preferably below 150 nm.

The Topical Compositions

The topical composition according to the present invention do not include an additional preservative.

Preservatives that are used in topical compositions include ammonium Benzoate, Butyl Benzoate, Calcium Benzoate, Ethyl Benzoate, Isobutyl Benzoate, Isopropyl Benzoate, Magnesium Benzoate, Mea-Benzoate, Methyl Benzoate, Phenyl Benzoate, Potassium Benzoate, Propyl Benzoate, Benzoic Acid, Sodium Benzoate, Propionic Acid, Ammonium Propionate, Calcium Propionate, Magnesium Propionate, Potassium Propionate, Sodium Propionate, Salicylic Acid, Calcium Salicylate, Magnesium Salicylate, Mea-Salicylate, Sodium Salicylate, Potassium Salicylate, Tea-Salicylate, Sorbic Acid, Calcium Sorbate, Sodium Sorbate, Potassium Sorbate (Hexa-2,4-Dienoic Acid And Its Salts), Formaldehyde, Paraformaldehyde, o-Phenylphenol, Mea o-Phenylphenate, Potassium o-Phenylphenate, Sodium o-Phenylphenate, Zinc Pyrithione, Sodium Sulfite, Ammonium Bisulfite, Ammonium Sulfite, Potassium Sulfite, Potassium Hydrogen Sulfite, Sodium Bisulfite, Sodium Metabisulfite, Potassium Metabisulfite, Chlorobutanol, Butylparaben, Propylparaben, Sodium Propoylparaben, Sodium Butylparaben, Potassium Butylparaben, Potassium Propylparaben (Butyl 4-Hydroxybenzoate and its salts) (Propyl 4-Hydroxybenzoate and its salts), 4-Hydroxybenzoic Acid, Methylparaben, Potassium Ethylparaben, Potassium Paraben, Sodium Methylparaben, Sodium Ethylparaben, Ethylparaben, Sidium Paraben, Potassium Methylparaben, Calcium Paraben, Dehydroacetic Acid, Sodium Dehydroacetate (3-Acetyl-6-Methylpyran-2,4(3H)-dione and its salts), Formic acid, Sodium Formate, Dibromohexamidine Isethionate (3,3'-Dibromo-4,4'-Hexamethylenedioxydibenzamidine and its salts (including Isethionate)), Thimerosal, Phenyl Mercuric Acetate, Phenyl Mercuric Benzoate, Undecylenic Acid, Potassium Undecylenate, Sodium Undecylenate, Calcium Undecylenate, Mea-Undecylenate, Tea-Undecylenate, Hexetidine (5-Pyrimidinamine, 1,3-Bis(2-Ethylhexyl)Hexahydro-5-Methyl-), 5-Bromo-5-Nitro-1,3-dioxane, 2-Bromo-2-Nitropropane-1,3-diol, Dichlorobenzyl alcohol, Triclocarban (1-(4-Chlorophenyl)-3-(3,4-Dichlorophenyl)Urea), p-Chloro-m-Cresol, Triclosan (5-Chloro-2-(2,4-Dichlorophenoxy)Phenol), Chloroxylenol, Imidazolidinyl Urea (N,N"-Methylenebis[N'-[3-(Hydroxymethyl)-2,5-Dioxoimidazolidin-4-Yl]Urea]), Polyaminopropyl Biguanide (Poly(Hexamethylenebiguanide) Hydrochloride; Poly(iminoimidocarbonyl)iminohexamethylene Hydrochloride; Poly (iminocarbonimidoyliminocarbonimidoylimino-1,6-Hexanediyl)), Phenoxyethanol, Methenamine, Quaternium-15 (Methenamine 3-Chloroallylochloride), Climbazole (1-(4-Chlorophenoxy)-1-(Imidazol-1-yl)-3,3-Dimethylbutan-2-one), DMDM Hydantoin (1,3-Bis(Hydroxymethyl)-5,5-Dimethylimidazolidine-2,4-dione), Benzyl alcohol, 1-Hydroxy-4-Methyl-6-(2,4,4-Trimethylpentyl)-2 Pyridon and its Monoethanolamine salt, Bromochlorophene (2,2'-Methylenebis(6-Bromo-4-Chlorophenol)), o-Cymen-5-ol (4-Isopropyl-M-Cresol), Methylchloroisothiazolinone and Methylisothiazolinone (Mixture of 5-Chloro-2-Methyl-Isothiazol-3(2H)-one and 2-Methylisothiazol-3(2H)-one with Magnesium Chloride and Magnesium Nitrate), Chlorophene (2-Benzyl-4-Chlorophenol), Chloroacetamide (2-Chloroacetamide), Chlorhexidine, Chlorhexidine Diacetate, Chlorhexidine Digluconate, Chlorhexidine Dihydrochloride (N,N'-Bis(4-Chlorophenyl)-3,12-Diimino-2,4,11,13-Tetraazatetradecanediamidine and its Digluconate, Diacetate and Dihydrochloride), Phenoxyisopropanol (1-Phenoxypropan-2-ol), Cetrimonium Bromide, Cetrimonium Chloride, Laurtrimonium Bromide, Laurtrimonium Chloride, Steartrimonium Bromide, Steartrimonium Chloride (Alkyl (C12-C22) Trimethyl Ammonium Bromide and Chloride), Dimethyl Oxazolidine (4,4-Dimethyl-1,3-Oxazolidine), Diazolidinyl Urea (N-(Hydroxymethyl)-N-(Dihydroxymethyl-1,3-Dioxo-2,5-Imidazolidinyl-4)-N'-(Hydroxymethyl) Urea), Hexamidine, Hexamidine Diisethionate, Hexamidine Diparaben, Hexamidine Paraben (Benzenecarboximidamide, 4,4'-(1,6-Hexanediylbis(Oxy))Bis-, and its salts (including Isothionate and p-Hydroxybenzoate)), Glutaral (Glutaraldehyde (Pentane-1,5-dial)), 7-Ethylbicyclooxazolidine (5-Ethyl-3,7-Dioxa-1-Azabicyclo[3.3.0] Octane), Chlorphenesin (3-(p-Chlorophenoxy)-Propane-1,2-Diol), Sodium Hydroxymethylglycinate, Silver Chloride, Benzethonium Chloride (Benzenemethanaminium, N,N-Dimethyl-N-[2-[2-[4-(1,1,3,3,-Tetramethylbutyl)Phenoxy] Ethoxy]Ethyl]-, Chloride), Benzalkonium Chloride, Benzalkonium Bromide, Benzalkonium Saccharinate, Benzylhemiformal (Methanol, (Phenylmethoxy)-), Iodopropynyl Butylcarbamate (3-Iodo-2-Propynylbutylcarbamate), Methylisothiazolinone (2-Methyl-2h-Isothiazol-3-one), Ethyl Lauroyl Arginate HCl, Citric Acid (and) Silver Citrate (1,2,3-Propanetricarboxylic acid, 2-Hydroxy-, Monohydrate and 1,2,3-propanetricarboxylic acid, 2-Hydroxy-Silver(1+) salt, Monohydrate).

In an embodiment of the present invention, the topical compositions or nanoemulsions according to the present invention do not contain an additional detergent or surfactant other than the quaternary ammonium salt surfactant. These additional detergents or surfactants may be characterized by having a HLB value ranging from 13 to 15 as calculated using the method described at A Quantitative Kinetic Theory of Emulsion Type. I. Physical Chemistry of the Emulsifying Agent, Davies, Gas/Liquid and Liquid/Liquid Interfaces Proceedings of 2nd Congress Surface Activity, Butterworths, London 1957.

In one embodiment, the topical composition further includes cosmetically active agent. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the cosmetically active agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, and soy, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs (such as vitamin B3, vitamin B5, and vitamin B12), vitamin C, vitamin K, and vitamin E, and derivatives thereof.

In one embodiment, the composition also contains one or more antioxidants. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions of this invention include, but are not limited to, butylated hydroxytoluene, tocopherols (e.g., tocopheryl acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612-13 of the ICI Handbook.

Topical Uses

Topical uses of the nanoemulsions and compositions of this invention are for diseases of the skin such as eczema, inflammation, and skin atrophy. The compositions of this invention are also used to stop, prevent, slow or inhibit the growth of biofilms of bacteria related to skin diseases.

As used herein, "topical use" and "topically applying" means directly laying on or spreading on the skin, hair, or nail, e.g., by use of the hands or an applicator such as a wipe.

EXAMPLES

The examples are to further illustrate the nature of the invention and the manner of carrying it out. However, the invention should not be considered as being limited to the details thereof.

The following materials and test methods were used in the Examples.

1. Materials & Methods 1.1 Formulation

The standard base formulation compositions are detailed in Table 1. The surfactant and emollient are selected from the list provided in paragraph 1.2 below. Each surfactant or emollient of the formulation may contain one or a combination of different products in each component category.

TABLE 1

Formulations of the compositions, for each component, in weight % of the total formula.

|  | Formula 1 | Formula 2 | Formula 3 |
|---|---|---|---|
| Glycerin | 5% | 12% | 12% |
| Surfactant | 1% | 5% | 2.5% |

TABLE 1-continued

Formulations of the compositions, for each component, in weight % of the total formula.

|  | Formula 1 | Formula 2 | Formula 3 |
|---|---|---|---|
| Emollient | 8% | 10.75% | 9.45% or 10.7% |
| NaCl | 0.2% | 0.01% | 0.01% |
| Water | qs to 100% | qs to 100% | qs to 100% |

1.2 Components of the Formulations
1.2.1 Surfactant
INCI name: Potassium Cetyl phosphate, Hydrogenated Palm Glycerides; Trade name:
Emulsiphos 677660; Provider: Symrise AG
INCI name: Distearyldimonium Chloride, isopropyl alcohol; Trade name: Varisoft TA100; Provider: EVONIK GOLDSCHMIT GmbH
INCI name: Behentrimonium Chloride, Dipropylene glycol; Trade name: Genamin BTLF; Provider: Clariant GmbH
INCI name: Triceteareth-4 Phosphate, ceteareth 4, cetearyl alcohol; Trade name: Hostaphat KW 340 D; Provider: Clariant International Ltd
1.2.2 Emollient
INCI name: Microcrystalline Wax; Paraffin; Mineral Oil; BHT, Trade name: Vaseline Blanche Codex Syntadex 7702, Provider: Synteal
INCI name: Isopropyl palmitate, Trade name: Isopropyl Palmitate, Provider: Cognis
INCI name: Dimethicone, Trade name: Element14 PDMS 10-A, Provider: EIGENMANN & VERONNELLI S.P.A
INCI name: Cetyl alcohol, Trade name: Lanette 16, Provider: BASF Personal Care & Nutrition GmbH
INCI name: Caprylyl glycol, trade name Dermosoft Octiol, provider Oxyrane Chemical Co. Ltd.
1.3 Microbiology
1.3.1 Challenge Test
Challenge tests are performed according to standard ISO11930 (2012). Challenge tests are based on inoculation of the formulation with calibrated inocula. The number of surviving micro-organisms is measured at defined intervals during a period of 28 days. For each time and each strain, the log reduction value is determined using calculated log challenge control count (inoculum density per gram at the starting point) vs log of recovery at different time points. Challenge tests are considered as a mild success if the log reduction is between 2 and 3; as a clear success if the log reduction is above 3.

The tests are run using the following strains as test micro-organisms:
*Pseudomonas aeruginosa* ATCC®9027TM2;
*Staphylococcus aureus* ATCC®6538TM;
*Escherichia coli* ATCC®8739TM;
*Candida albicans* ATCC®10231TM;
*Aspergillus brasiliensis* (previously *A. niger*) ATCC®16404TM.

The tests are done in sterile capped bacteriological containers. A minimum of 20 g of test material is transferred into the sterile container. The product is thoroughly mixed for approximately 1 minute immediately after inoculation. Inoculated samples are stored at 20° C. during the test period. Before each sampling, the products are carefully mixed to ensure homogeneity. Plate count serial dilutions are performed in neutralizer to neutralize the preservative system. The minimum sample size is 1 ml/gram for standard products+9 ml neutralizer. Microorganisms are grown on agar plates using TSA or SDA incubation media, for 4 days at 30° C. or 20° C. After incubation, the number of microbial colonies is counted and the average cfu/ml for duplicate plates is multiply by the dilution factor.

1.3.2 Biofilm Growth, Crystal Violet Method
Experiments on biofilm growth were performed according to the protocol disclosed in G. A. O'Toole, *Microtiter Dish Biofilm Formation Assay, J Vis Exp.* 2011; (47): 2437. The protocol disclosed by G. A. O'Toole teaches the assay on *Pseudomonas aeruginosa*, it was adapted to *Staphylococcus Aureus* MFP03 and *Staphylococcus Epidermis* MFP04.

Two conditions were studied:
The effect of the emulsions on biofilms in formation: the emulsions are added to the medium from the beginning of the bacterial growth.
The effect of emulsions on established biofilms: the emulsions are added to the bacteria after a first 24-hour incubation that allowed the development of the biofilm.

The protocol taught by G. A. O'Toole is as follows:
Growing a Biofilm
1. Grow a culture of the wild-type *Pseudomonas aeruginosa* or mutant strain overnight in a rich medium (i.e. LB)
2. Dilute the overnight culture 1:100 into fresh medium for biofilm assays. A standard biofilm assay medium for *P. aeruginosa* is M63 minimal medium supplemented with magnesium sulfate, glucose and casamino acids. As an alternative biofilm-promoting medium that stimulates less planktonic growth and a more robust biofilm, the glucose and casamino acids can be replaced with arginine as the sole carbon and energy source.
3. Add 100 µL of the dilution per well in a 96 well dish. For quantitative assays, we typically use 4-8 replicate wells for each treatment.
4. Incubate the microtiter plate for 4-24 hrs at 37° C.

Staining the Biofilm
1. After incubation, dump out cells by turning the plate over and shaking out the liquid.
2. Gently submerge the plate in a small tub of water (i.e., use the bottoms of pipette tip boxes for P1000 pipetmen as the tub). Shake out water. Repeat this process a second time. This step helps remove unattached cells and media components that can be stained in the next step, and significantly lowers background staining.
3. Add 125 µL of a 0.1% solution of crystal violet in water to each well of the microtiter plate.
4. Incubate the microtiter plate at room temperature for 10-15 min.
5. Rinse the plate 3-4 times with water by submerging in a tub of water as outlined above, shake out and blot vigorously on a stack of paper towels to rid the plate of all excess cells and dye.
6. Turn the microtiter plate upside down and dry for a few hours or overnight.
7. For qualitative assays, the wells can be photographed when dry.

Quantifying the Biofilm
1. Add 125 µL of 30% acetic acid in water to each well of the microtiter plate to solubilize the CV.
2. Incubate the microtiter plate at room temperature for 10-15 min.
3. Transfer 125 µL of the solubilized CV to a new flat bottomed microtiter dish.
4. Quantify absorbance in a plate reader at 550 nm using 30% acetic acid in water as the blank.

For the conditions of biofilms in formation: emulsions at 10% (w/w) are added to the medium, and after 24 h of incubation, the optical density is measured. For established biofilms: after 24 hours of biofilm growth, the culture medium was eliminated and replaced for 4 hours by emulsion. Optical density is then measured. Results are expressed in percentage of absorbance relative to the control sample, which is the biofilm itself. For biofilms in formation, a decrease in this percentage represents the growth inhibition in the presence of the emulsion. For established biofilms, a decrease in this percentage represents an impact on already established biofilms.

1.3.3 Biofilm Growth Inhibition, Wells Method.

Experiments on biofilm growth were performed according to the protocol disclosed in Hui Zhang et al., *Characterization and antimicrobial activity of a pharmaceutical microemulsion*, International Journal of Pharmaceutics 395 (2010) 154-160.

Protocol disclosed by Hui Zhang was adapted as follow:
a—100 μL of a bacterial strains culture ($DO_{580}$=0.5) is spread on a LB culture plate.
b—5 mm diameter wells are created with a punch in the gel surface of the culture plate. Each well is attributed to one formulation, the same formulation throughout the test.
c—50 μL of tested formulation is injected per well.
d—24 hours incubation at 37° C.
e—Wells are emptied from the formulations.
f—Growth inhibition halos are measured.
g—Repeat from step c to obtain data over several days (8 days in the present case).

1.4 Nano Emulsion 1.4.1 Apparatus

Microfluidizer M110P, Hydraulic intensifier pump and F12Y interaction chamber are manufactured by Microfluidics (Westwood, Mass.).

1.4.2 Emulsion Preparation

The emulsions are prepared in the lab per the following process:

In the main vessel, purified water is introduced and heated to 50° C. under stirring with a mixer such as Turbotest from VMI Raynerie. Then sodium chloride is added under stirring. The mixture is heated to 80° C. Then, the surfactants and the emollients are successively added under stirring and mixed until complete dissolution. The mixture is cooled down to 60° C. Around 60° C., the glycerin is added under stirring. The process is ended at 60° C.

1.4.3 Nano Emulsion Preparation

The nanoemulsions are prepared according to a high-pressure microfluidic process. The coarse emulsion, at 50° C. enters the system via the inlet reservoir of the Microfluidics M110P machine. The emulsion is then powered by 20,000 psi pressure generated by the hydraulic intensifier pump. M110P propels product through the F12Y interaction chamber. The product is accelerated to a high velocity and subjected to intense shear and impact (velocity, shear and impact are inherent characteristics of the machine with the interaction chamber). 6 mL of product passes through the chamber in less than a second, fluids have to travel through the chamber at over 300 m/s. After processing, the product is collected in the output reservoir. Unless otherwise specified, the emulsion is submitted to this process for three passes.

1.4.4 Droplets Size

Droplets sizes are measured by the Mastersizer 3000 (Malvern Instruments Ltd, UK) with dynamic light scattering technique by measuring the angular variation in intensity of light scattered as a laser beam passes through a dispersed particulate sample.

The nanoemulsion droplets are measured according the following process:
Demineralized water should be taken the day before to get tempering and gas free water for the experiment
The equipment is started 20 min before analysis
The circulation loop is rinsed with normal water (it eases the cleansing), then one time with demineralized water
Parameters of analysis are:
    Refraction index: 1.450
    Absorption index: 0.001
    Mie theory
    Model: spherical
    Acquisition time in the red wavelength: 10 s+10 s of background
    Acquisition time in the blue wavelength: 3 s+3 s of background
    5 measurements
    No waiting time between and before measurement
Speed stirring: 1500 rpm
Initialization
    Detector 1<100
    Detector 20<20
    The detection diagram profile must be a regular decreasing exponential without bumps
    Power must be in the green area
Background until signal is poor and randomly oscillating
Sample preparation:
    A small quantity of product (point of spatula) is diluted in about 2 drops of purified water until homogeneous
    About 2 ml of additional water are added and stirred manually until the mixture is homogeneous
    When it is homogeneous, this dilution is introduced with a pipette directly at the bottom of the sampler until an obscuration of about 5%. When obscuration is stable, start the measurement. Repeat the measurement until getting RSD values below 5% (steady curves for d10, d50 and d90).
Acceptance criteria:
    10 points are required. RSD must be <5%
    Residual and weighted residual must be <2%
    Fits acceptable signal must be 3 times higher than the background noise.

Nanoemulsions have small-sized droplets having greater surface area as compared to regular emulsions droplets. Reducing the droplet radius multiplies the surface area. The Sauter diameter D[3;2] is the diameter used to characterize these droplets. It is defined as the diameter of a sphere that has the same volume/surface area ratio as a particle of interest and is sensitive to small particles.

1.5 Viscosity

The viscosity measurements were performed on a Physica MCR 300 (Anton Paar GmbH) at a shear rate of 45 $s^{-1}$.

Test method:
Set according to the supplier recommendation.
Realize a motor adjustment, initialization and Zero Gap.
Put the thermostat on at 20° C. The measuring/sample temperature should be 20° C.
Use a Microman pipette to take the volume of product corresponding to the cone/plate gap of your equipment+10%
Slowly release the product on the center of the plate without moving. It must create a symmetric round volume. Avoid bubble formation.

Move downward the cone to the measuring position depending on the Truncation viscosity at a shear-rate of 45 s$^{-1}$ Then apply the following protocol to get the viscosity at 45 s$^{-1}$:
1. Set-up at 20° C. during 120 sec. No shear rate.
2. 3 measures every 10 sec at 5 s−1
3. 9 measures every 4 sec during increase from 5 s$^{-1}$ to 45 s$^{-1}$
4. 2 measures every 5 sec at 45 s$^{-1}$ The value to be recorded for viscosity is the second measure at 45 s$^{-1}$.

2. Examples and Test Results

2.1 Challenge Tests

Five compositions (Examples 1 to 5) were tested for their microbiological stability per the challenge test protocol described above. None of these compositions was submitted to microfluidization. Purpose was to select the most efficient surfactant with respect to the challenge test.

Example 1 (Comparative Example)

Composition of Example 1 was formulated according to formula 1.

Surfactant was Potassium Cetylphosphate, 1% of the formula total weight.

Example 2 (Comparative Example)

Composition of Example 2 was formulated according to formula 2.

Surfactant was Triceteareth-4 Phosphate, 5% of the formula total weight; and Cetyl alcohol 1.25% of the formula total weight.

Example 3 (Comparative Example)

Composition of Example 3 was formulated according to formula 2.

Surfactant was Distearyl dimmonium Chloride, 5% of the formula total weight; and Cetyl alcohol 1.25% of the formula total weight.

Example 4 (Comparative Example)

Composition of Example 4 was formulated according to formula 2.

Surfactant was Behentrimonium Chloride, 5% of the formula total weight; and Cetyl alcohol 1.25% of the formula total weight.

Example 5 (Comparative Example)

Composition of Example 5 was formulated according to formula 2.

Surfactant was Behentrimonium Chloride, 5% of the formula total weight; and Cetyl alcohol 2.5% of the formula total weight.

Compositions of Examples 1 and 2 failed the challenge test except for *E. Coli* for Example 2. Microbiological growth was observed. Composition of Example 3 succeeded the challenge test but failed over *C. albicans* and *A. brasiliensis*. Compositions of Examples 4 and 5, succeeded the challenge test. Composition of example 5 narrowly missed the test over *A. brasiliensis*, whereas the composition of example 4 was a mild success. Detailed results are presented in Table 2.

TABLE 2

Challenge test of the comparative example formulations, after 28 days, expressed in log reduction

| 28 days | E. coli | S. aureus | P. aeruginosa | C. albicans | A. brasiliensis |
|---|---|---|---|---|---|
| Example 1 | −0.7 | 1.6 | 0.2 | −0.8 | 0.3 |
| Example 2 | 2.1 | 0.6 | 1.2 | −0.7 | 0.0 |
| Example 3 | 3.7 | 3.8 | 3.8 | −1 | 1.0 |
| Example 4 | 3.5 | 3.6 | 3.5 | 3.5 | 2.4 |
| Example 5 | 3.7 | 3.9 | 3.5 | 3.5 | 1.8 |

Behentrimonium Chloride proved to be superior to the other three surfactants tested as for the challenge test.

2.2 Nanoemulsions—Challenge Test

Compositions according to examples 4 and 5 were submitted to microfluidization according to the protocol described above to obtain nanoemulsions (examples 6 and 7 respectively).

Example 6

Composition of Example 6 was formulated the same way as in example 4. Further, the composition of example 6 was submitted to microfluidization.

Droplet Sauter diameter D[3;2]: 60 nm, at t=0 and after 3 months.

Example 7

Composition of Example 7 was formulated the same way as in example 5. Further, the composition of example 7 was submitted to microfluidization.

Both compositions of Examples 6 and 7, succeeded the challenge test. Composition of Example 7 showed results even superior to its counterpart that was not submitted to microfluidization (namely Example 5), against *A. brasiliensis*.

Detailed results are presented in Table 3.

TABLE 3

Challenge test of formulations according to the invention vs comparative example formulations, after 28 days, expressed in log reduction.

| 28 days | E. coli | S. aureus | P. aeruginosa | C. albicans | A. brasiliensis |
|---|---|---|---|---|---|
| Example 4 | 3.5 | 3.6 | 3.5 | 3.5 | 2.4 |
| Example 5 | 3.7 | 3.9 | 3.5 | 3.5 | 1.8 |
| Example 6 | 3.5 | 3.6 | 3.5 | 3.7 | 2.2 |
| Example 7 | 3.7 | 3.9 | 3.5 | 3.5 | 2.1 |

Behentrimonium nanoemulsions proved to be as efficient as their equivalents not submitted to microfluidization.

2.3 Impact on Biofilms

Compositions according to examples 6 and 7 (invention) were tested on *Staphylococcus aureus* biofilms according to the crystal violet methodology disclosed on paragraph 1.3.2. Tests were repeated on biofilms in formation and established biofilms. Compositions according to examples 4 and 5 (Comparative examples) were submitted to the same growth inhibition tests, to assess the effect of the microfluidization. A 10% solution of Triton X-100 (Aldrich) was submitted to the same test as a benchmark. Detailed results are presented in Table 4.

TABLE 4

Effect of microfluidization on the development of bacterial strains biofilms under formation and established; expressed in absorbance percentage, relative to the control, which is the biofilm itself.

|  | Bacterial strain S. aureus | |
| --- | --- | --- |
| Biofilm | In formation | Established |
| Example 4 | 298 | 224 |
| Example 5 | 219 | 168 |
| Example 6 | 1 | 36 |
| Example 7 | 22 | 35 |
| Triton | 27 | 177 |

Compositions according to examples 6 and 7 both showed good to excellent inhibition of biofilm growth for biofilms in formation on both bacterial strains and showed a strong impact on established biofilms of both strains. These results are clearly superior to the equivalent compositions not submitted to microfluidization; and superior to the Triton reference.

2.4 Droplets Size

Different microfluidization parameters were tested to see the influence of the nanoemulsion droplets size on growth inhibition of bacterial strains biofilms, in formation or established.

Example 8

The composition of Example 8 was formulated the same way as in example 6. The composition of Example 8 was submitted to microfluidization (1 pass, 20,000 psi). Droplet Sauter diameter D[3;2]: 120 nm, at t=1 Month

TABLE 5

Effect of the nanoemulsion droplets diameter on the development of bacterial strains biofilms under formation and established; according to the crystal violet methodology disclosed on paragraph 1.3.2, expressed in absorbance percentage, relative to the control, which is the biofilm itself.

|  | Bacterial strain S. aureus | |
| --- | --- | --- |
| Biofilm | In formation | Established |
| Example 6 | 1 | 36 |
| Example 8 | 55 | 208 |

Example 8 is less effective than Example 6 on biofilms in formation or established. Example 8 has activity on the inhibition of biofilms, but is not as efficient on the impact of established biofilms as other composition according to the present invention. Nanoemulsion droplets seem to be more efficient on the impact of established biofilm, if their Sauter diameter is below 120 nm.

2.5 Antimicrobial Activity on Biofilms; Comparison Between S. Aureus and S. Epidermidis Two compositions (Examples 10 and 12) were tested for their growth inhibition activities against Staphylococcus Aureus and Staphylococcus Epidermidis biofilms.

Example 9 (Comparative Example)

Composition of Example 9 was formulated according to formula 3. Surfactant was Behentrimonium Chloride, 2.5% of the formula total weight; Emollients were 10.7% of the total weight, including: Cetyl alcohol 2.5% of the formula total weight; and Caprylyl glycol, 0.2% of the formula total weight.

Example 10

Composition of Example 10 was formulated the same way as in example 9. Further, the composition of example 10 was submitted to microfluidization. Droplet Sauter diameter D[3;2]: 126 nm, at t=0 and after 3 months.

Example 11 (Comparative Example)

Composition of Example 11 was formulated according to formula 3. Surfactant was Behentrimonium Chloride, 2.5% of the formula total weight; Emollients were 9.45% of the total weight, including: Cetyl alcohol 1.25% of the formula total weight; and Caprylyl glycol, 0.2% of the formula total weight. Droplet Sauter diameter D[3;2]: 36 µm, at t=0 and after 3 months.

Example 12

Composition of Example 12 was formulated the same way as in example 11. Further, the composition of example 12 was submitted to microfluidization. Droplet Sauter diameter D[3;2]: 52 nm, at t=0 and after 3 months.

2.5.1 Challenge Tests for Compositions According to Examples 9 to 12

Compositions according to examples 9, 10 and 12 succeeded the challenge test. Composition according to example 11 was not stable; the tests were not conducted.

Detailed results are presented in Table 6.

TABLE 6

Challenge test of formulations according to the invention vs comparative example formulation, after 28 days, expressed in log reduction.

| 28 days | E. coli | S. aureus | P. aeruginosa | C. albicans | A. brasiliensis |
| --- | --- | --- | --- | --- | --- |
| Example 9 (comparative) | 3.9 | 3.7 | 3.4 | 3.7 | 3.6 |
| Example 10 | 3.9 | 3.7 | 3.4 | 3.7 | 3.6 |
| Example 12 | 3.6 | 3.5 | 3.6 | 3.3 | 3.7 |

2.5.2 Impact on Biofilms, Crystal Violet Method

Compositions according to examples 10 and 12 were tested on Staphylococcus aureus biofilms and Staphylococcus Epidermidis biofilms. Tests were conducted on biofilm under formation and on established biofilms, according to the methodology disclosed on paragraph 1.3.2 (Crystal violet). Detailed results are presented in Table 7.

TABLE 7

Effect of the nanoemulsions according to examples 10 and 12, on the development of bacterial strains biofilms under formation and established; according to the crystal violet methodology disclosed on paragraph 1.3.2 expressed in absorbance percentage, relative to the control, which is the biofilm itself.

|  | Bacterial strain | | | |
| --- | --- | --- | --- | --- |
|  | S. Aureus | | S. Epidermidis | |
| Biofilm | In formation | established | In formation | established |
| Example 10 | 60.51 | 83.04 | 48.96 | 114.9 |
| Example 12 | 3.9 | 14.68 | 3.72 | 21.54 |

Formulations according to example 10 and 12 show a growth inhibition on both S Aureus and S. Epidermidis biofilm. Formulation according to example 12 seems to be more efficient than the formulation according to example 10. Both are more efficient on biofilm under formation than established biofilm.

2.5.3 Impact on Biofilms, Wells Method.

Compositions according to examples 10 and 12 (invention) were tested on *Staphylococcus aureus* biofilms and *Staphylococcus Epidermidis* biofilms. Tests were conducted on biofilms according to the methodology disclosed on paragraph 1.3.3 (Wells). A 10% solution of Triton X-100 (Aldrich) was submitted to the same test, results after 2 days were used as references.

Inhibition halos were measured and compared to the inhibition halo obtained for the Triton X-100 solution after 2 days. Inhibition halo differences are expressed in %. Over 100% the inhibition is higher than what is observed for Triton at 2 days; under 100% the inhibition is lower than what is observed for Triton at 2 days. Inhibition was measured at 2 days and 8 days.

Detailed Results are Presented in Table 8.

TABLE 8

Effect of formulations on the development of *S. Aureus* and *S Epidermidis* bacterial strains biofilms; expressed in growth inhibition %, relative to Triton X-100 at 2 days.

| | Bacterial strain | | | |
|---|---|---|---|---|
| | S. Aureus | | S. Epidermidis | |
| | 2 days | 8 days | 2 days | 8 days |
| Example 10 | 3.6 | 4.8 | 0 | 0 |
| Example 12 | 47.8 | 93.3 | 0 | 0 |
| Triton X-100 | 100 | 198.5 | 100 | 231 |

Surprisingly, the formulation according to example 12 showed a growth inhibition of biofilms of *S Aureus*, but no inhibition for *S Epidermidis* biofilms. This selectivity is highly desirable and could help balance the skin microbiome and improve atopic dermatitis conditions. Difference of inhibitions between formulations according to example 10 and 12, in view of table 7 and 8, may be explained by the differences in viscosity. Formulation according to example 12 is more fluid than formulation according to example 10 (see table 9), this may result in a better permeation through the gel used in the wells methodology (see paragraph 1.3.3). It may also be possible to interpret this result in view of paragraph 2.4; the nanoemulsion particle diameter is higher for Example 10 (126 nm) than for example 12 (52 nm).

2.6 Viscosity

Viscosities of the compositions according to the examples of the present invention were measured using the process described in paragraph 1.5.

TABLE 9

Viscosity of the compositions according to the examples of the present invention.

| Emulsion | Viscosity (cP) at 45 s$^{-1}$ |
|---|---|
| Example 1 (Comparative example) | 2050 |
| Example 2 (Comparative example) | N/A (liquid) |
| Example 3 (Comparative example) | 575 |
| Example 4 (Comparative example) | 502 |
| Example 5 (Comparative example) | 1320 |
| Example 6 | N/A (liquid) |
| Example 7 | 359 |
| Example 8 | 123 |
| Example 9 (Comparative example) | 1050 |
| Example 10 | 664 |
| Example 12 | 15 |

Examples 6, 7, 8, 10 and 12 all have a low viscosity value below 700 cP at 45 s$^{-1}$, even below 360 cP at 45 s$^{-1}$ for examples 6, 7, 8 and 12. Droplets size seems to have a correlation with fluidity (see examples 7 & 8). Low viscosity could be advantageous when applying a composition on a damaged skin or mucosa, by avoiding a mechanical action to spread the composition, for example the composition may be conditioned in a spray or a roll-on stick.

While the invention has been described above regarding specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

The invention claimed is:

1. A topical composition comprising an oil in water nanoemulsion wherein said nanoemulsion comprises
    behentrimonium chloride, wherein said behentrimonium chloride is present in an amount from about 2% to about 5% by weight of the composition,
    glycerin, wherein said glycerin is present in an amount from about 5% to about 15% by weight of the composition;
    a water phase; and
    cetyl alcohol, wherein said cetyl alcohol is present in an amount 0.5% to about 5% by weight of the composition,
    wherein said nanoemulsion comprise droplets having a Sauter diameter D[3;2] between about 52 nm to about 60 nm.

2. The topical composition according to claim 1, wherein said composition is free of additional surfactants.

3. The topical composition according to claim 1, wherein said nanoemulsion comprises droplets having a Sauter diameter D[3;2] of about 52 nm.

4. The topical composition according to claim 1, wherein the topical composition comprises about 5% to about 15% by weight of water based on total weight of the topical composition.

5. The topical composition according to claim 1, comprising about 50% to about 90% by weight of water based on total weight of the topical composition.

6. The topical composition according to claim 1, wherein said composition is free of a preservative.

7. A method of killing or inhibiting the growth of bacteria in a biofilm comprising exposing a biofilm to the nanoemulsion according to claim 1.

8. The method of claim 7, wherein the bacteria in the biofilm is *Staphylococcus aureus*.

* * * * *